United States Patent [19]
Chaney

[11] Patent Number: 5,779,621
[45] Date of Patent: Jul. 14, 1998

[54] PENILE RING GAUGE

[76] Inventor: John L. Chaney, 156 Broad St. Box 790, Lake Geneva, Wis. 53147

[21] Appl. No.: 739,414

[22] Filed: Oct. 29, 1996

[51] Int. Cl.$^6$ ........................................... A61F 5/00
[52] U.S. Cl. ........................ 600/38; 600/41; 33/512; 33/555.4
[58] Field of Search .................. 600/38, 39, 41; 33/511, 512, 514.1, 514.2, 555.4; 128/774

[56] References Cited

U.S. PATENT DOCUMENTS

| | | | |
|---|---|---|---|
| 4,433,486 | 2/1984 | Muehlenbein | 33/555.4 |
| 4,539,980 | 9/1985 | Chaney | 600/41 |
| 4,875,296 | 10/1989 | Holzmeister et al. | 33/512 |
| 4,960,131 | 10/1990 | Koss | 128/774 |

*Primary Examiner*—Jennifer Bahr
*Assistant Examiner*—Rosiland Kearney
*Attorney, Agent, or Firm*—Ryan, Maki, Mann & Hohenfeldt, S.C.

[57] ABSTRACT

A gauge strip of flexible material having distal and proximal end portions has a cursor slot in its proximal end portion with graduation marks and penile constriction ring size indicia between the end portions for the distal end of the strip to be passed through the cursor slot to form a loop that is pulled tight on the penis for the cursor slot to coincide with an elastic ring size indicia that is read to select a ring or vacuum tube penis entry opening of the appropriate percentage of the penis size for developing an erection by vacuum exposure, maintaining an erection with the ring, or using the ring as a condom retainer.

9 Claims, 3 Drawing Sheets

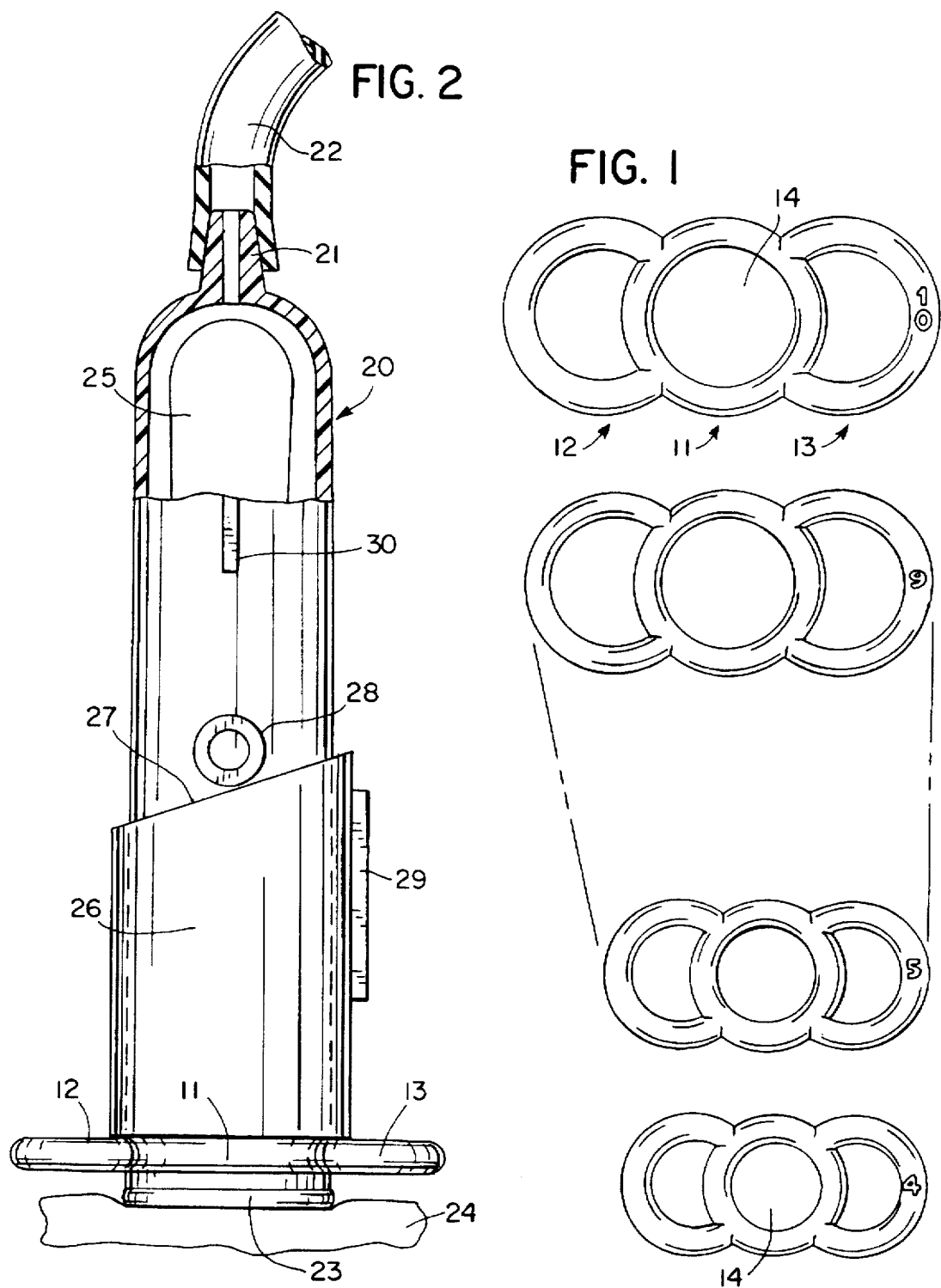

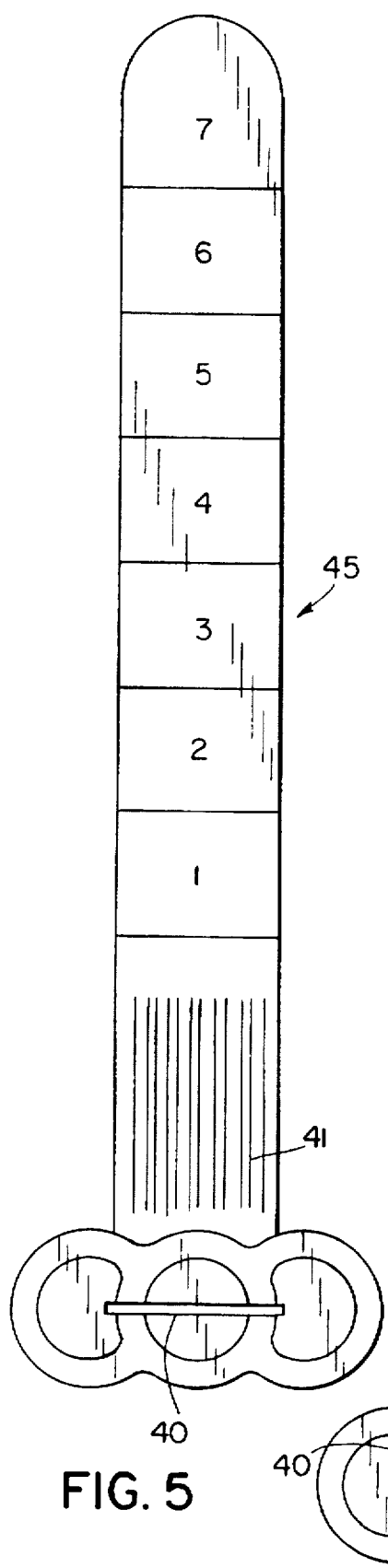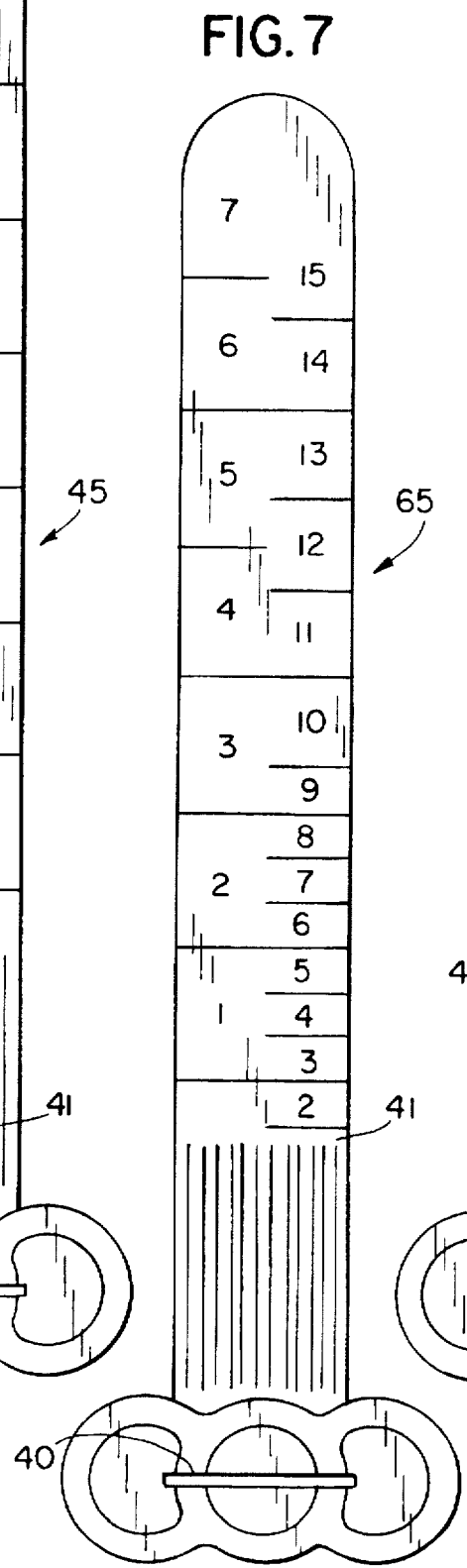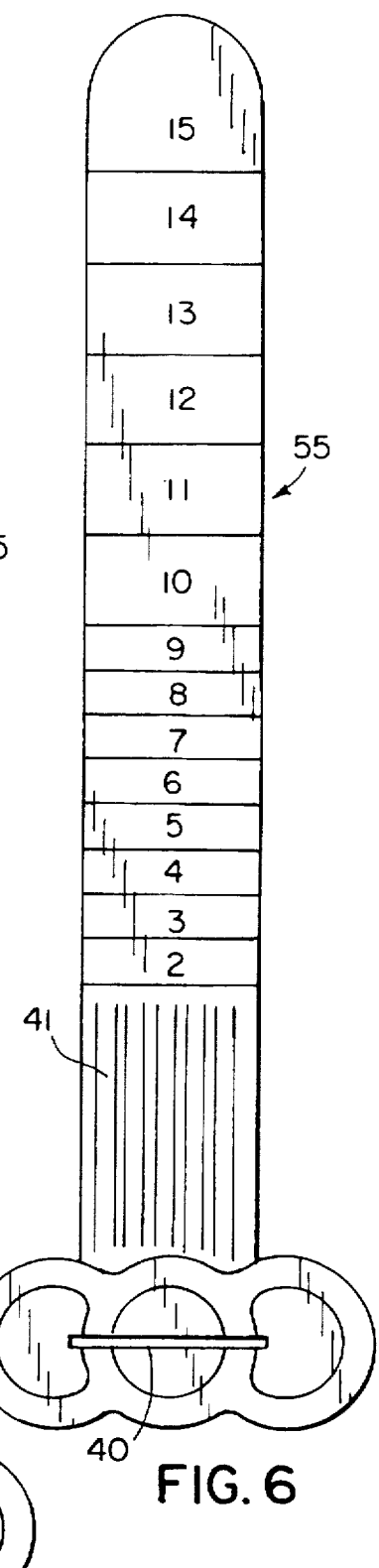

PENILE RING GAUGE

BACKGROUND OF THE INVENTION

The invention disclosed herein pertains to a set of gauges for determining the size of the elastic penile constriction ring that is appropriate for various penis erection achieving and maintaining procedures and for preventing a condom from slipping from the penis during intercourse to thereby assure safer sex.

An illustrative elastic penile constriction ring is disclosed in U.S. Pat. No. 4,539,980 which was granted on Sept. 10, 1985 to the inventor of the invention described herein. The patented constriction ring comprises a central ring of elastic material, such as latex, that has diametrically opposite loops joined with the periphery of the central ring so the central ring can be stretched using the loops for the ring to be passed over the penis to its base, after which the central ring is allowed to contract for modulating the flow of blood into and out of the penis in a manner that is similar to what occurs in nature and an erection is achieved by a male who is not totally impotent.

One way of using the ring described in the patent and rings of other designs as well is to install a ring having the appropriate size and elasticity on the base of the penis. A ring having the appropriate size and elasticity is one that contracts tightly enough on the penis to permit arterial blood to be forced into the penis to cause an erection while at the same time preventing venous blood from discharging from the penis. Actually, the appropriate constriction ring is one that has a central ring whose opening is a predetermined percentage of the penis diameter during the existence of an erection. Under these circumstances, an erection can be achieved and maintained. A central ring that is too large compared to the penis diameter will allow venous blood to leak out so even if an erection were obtained, the penis would become flaccid quickly. A central ring that is too small for the penis diameter may not only be uncomfortable for the user but may prevent arterial blood from being forced into the penis in which case an erection will not be achieved.

One method of achieving and maintaining an erection with an elastic penile ring is to apply a ring of appropriate elasticity to the base of the penis. This is followed by massaging blood along the scrotum to the base of the penis so that arterial blood can be forced into the penis while at the same time the elasticity of the ring is sufficient to prevent venous blood from escaping the penis, so that the arterial blood pressure and, hence, the erection will be maintained. The procedure involves applying a ring having an appropriate elastic characteristic over the base of the penis and then massaging the scrotum in the direction of the penis to overcome the elastic force of the central ring and cause an inflow of arterial blood. After an erection is achieved in this way, sexual intercourse can proceed.

Another method of achieving an erection and then maintaining an erection by using a constriction ring is known as vacuum therapy. According to this method, the flaccid penis is inserted into the end opening of a tube that can be evacuated. The tube is pressed tightly against the body circumjacent the penis to effect a seal and the tube is evacuated down to about 12 inches of mercury by use of a hand-operated vacuum pump. The penis expands in the vacuum ambient. Since arterial blood pressure is higher than the vacuum level in the tube, arterial blood is caused to flow into the penis. In preparation for carrying on this method, the constriction ring is put onto the vacuum tube before the tube is pressed against the body for being evacuated. When the erection is achieved, the ring is forced off the tube and onto the base of the penis for keeping the pressurized blood in the penis so that the erection is maintained.

Another use of a constriction ring is to prevent a condom from slipping from the penis after the penis becomes flaccid following completion of sexual intercourse. It is well known that the condom often slides off of the penis at termination of sexual intercourse in which case if one of the sexual partners has a transmissible disease, it may be transferred to the other of the partners by direct contact between the sexual organs of the two bodies. A constriction ring having appropriate characteristics can be used to prevent loss of the condom without the user experiencing any discomfort during intercourse while the penis is expanded and erect.

For all of the methods and procedures connected with obtaining and maintaining an erection as were described above, it is important to determine the relationship between the diameter of the penis and the constriction ring opening or the vacuum tube opening size that will correspond to a chosen percentage of the penis diameter. As implied above, the penis diameter during an erection must be known for the user to select the constriction ring having the appropriate size and elastic force for that person. As pointed out, for the massaging technique and vacuum therapy, the ring must be sized appropriately for allowing arterial blood to be forced into the penis and for preventing inadvertent outflow of venous blood from the penis. There is another problem associated with vacuum therapy, however. If when the penis is inserted in the vacuum tube the lip defining the opening of the tube has an inside diameter substantially greater than the diameter of the penis, the round rim of the tube will be encircling the base of the penis a substantial radial distance from the penis itself.

The consequence of this is that when the vacuum is created, the pubic hair and soft tissue surrounding the penis is drawn into the tube by the vacuum. This is known to be painful. Thus, it would be highly desirable to provide a constriction ring user with a means for gauging the size of the penis and thereby enabling selection of a vacuum therapy tube inlet opening which is not excessively greater than the diameter of the erect penis.

Some manufacturers of constriction rings have only three rings of different sizes in a set of rings which they provide to a potential user. In this case the diameter of one of the rings in the series or set differ substantially in diameter from the next ring in the series. The consequence of this is that in many cases the user cannot find a ring in the set that is just right for his penis size. The inventor of the present application has followed the practice of making available, to those who are handicapped by impotence, a set of seven constriction rings having central ring diameters that differ from each other in 1/16 inch steps. This raises the probability of a user being able to select the ring size that is exactly right for him.

A problem underlying selection of the correct ring size for massage and vacuum therapy, condom retention and selection of the vacuum tube size is the determination of the diameter of an erect penis. In some cases, potential users have simply made a rough estimate of the penis diameter. Others have resorted to measurement of the circumference of the penis at its base and then calculating the diameter by dividing the circumference by pi. Experience has shown, however, that most potential users have difficulty in arriving at the proper size of a ring or vacuum tube if ordinary judgment or mathematical calculation is required. In other words, it will be evident that the problem can be solved best by providing penis gauges which have a scale that can be read to provide a number that accurately relates the diameter of the penis to the size of the constriction ring and the size of the vacuum therapy tube that ought to be selected.

SUMMARY OF THE INVENTION

In accordance with the invention, gauges are provided for determining proper matching between the diameter of the penis and constriction ring or the vacuum therapy tube.

Each of the gauges comprises a strip of tough paper that has graduations marked along its length. Each strip has a distal end and a proximal end. There is a slot through the strip near the proximal end. The user selects the strip that is designed for either measuring the diameter of the penis for the purposes of massage or vacuum therapy or for condom retention or for determining vacuum tube size. The selected gauge is wrapped around the penis and the distal end is passed through the slot at the proximal end. The slot, in a sense, serves as a cursor. When the strip is pulled tight around the penis the graduation adjacent the slot is noted. The number that is read is then used to select the correspondingly numbered constriction ring which automatically provides a central ring whose diameter is some predetermined percentage of the diameter of the penis for massage and vacuum therapy, another percentage of the penis size for condom retention and another percentage of penis size for vacuum tube sizing.

How all of the foregoing general features of the invention and other more specific features are implemented, will appear in the more detailed description of a preferred embodiment of the invention which will now be set forth in reference to the accompanying drawings.

DESCRIPTION OF THE DRAWINGS

FIG. 1 depicts several constriction rings taken from a series of ten rings which have been used before the invention disclosed herein was made;

FIG. 2 is an elevational view, partly in section, of a vacuum impotence therapy tube as used to develop an erection, the tube having one of the constriction rings mounted to it that is selected from the series in FIG. 1 and is positioned on the vacuum tube for being slid off onto the base of the penis;

FIG. 5 is a plan view of a version of the new gauge that is used to assist in selecting the vacuum tube having a penis inlet opening size that is appropriate for the size of the penis determined by using the gauge;

FIG. 6 is a plan view of a version of the gauge that is used to select the elastic constrictor ring size which will cause a condom to be retained on the penis when it becomes flaccid after intercourse terminates; and FIG. 7 a plan view of a multifunctional gauge that is calibrated for determining the vacuum tube or penis inlet opening size and also calibrated for determining the elastic constrictor size that should be chosen for retaining a condom on the penis of a user after the penis becomes flaccid.

DESCRIPTION OF A PREFERRED EMBODIMENT

Figure 4:
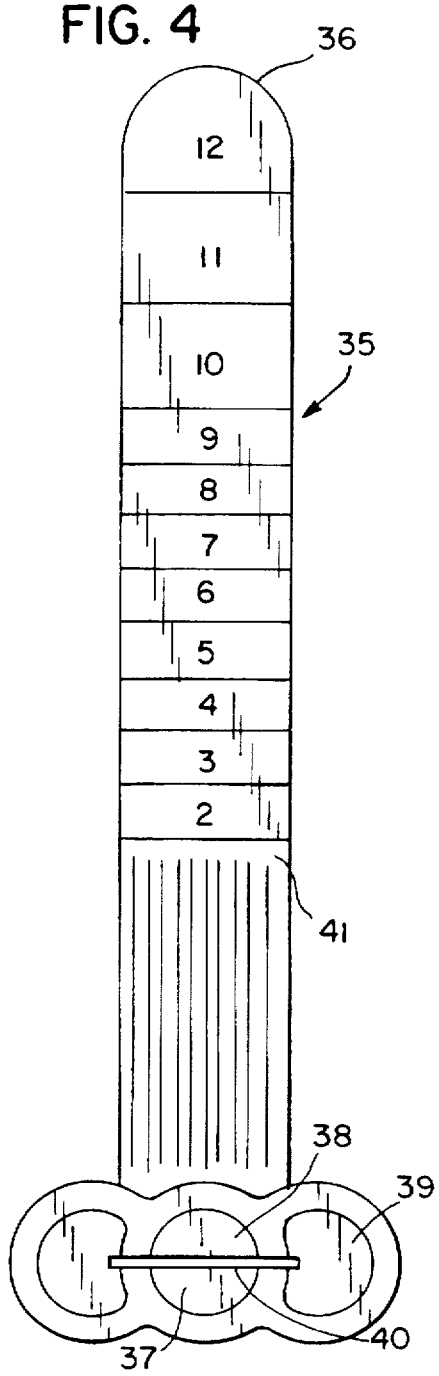
FIG. 4 is a plan view of a gauge that is similar to the gauge depicted in FIG. 3.

FIG. 1 shows a set of constrictor rings that are identified by the numbers 1-10. Constrictor rings of the design depicted in FIG. 1 are described in detail in U.S. Pat. No. 4,539,980 which is owned by the inventor in the present application. A typical one of the constrictor rings marked 10 is comprised of a central ring 11 having integral lateral loops 12 and 13. As described in the patent, the loops are useful for stretching and expanding the central ring 11 to permit the central ring to be slid to the base of the penis after which the loops are released and the elasticity of the central ring acts as to modulate inflow of arterial blood to the penis when blood is massaged into the penis or is caused to enter by having the penis in a vacuum ambient. The central ring and loops are preferably molded as a single piece using an elastic material such as natural or synthetic latex. The central ring 11 is usually round in cross-section. The elastic force which the central ring can apply to the penis depends, of course, on the cross-sectional diameter of the central ring and the material of which it is made. For the sake of uniformity and to facilitate use of the gauges to be described herein, the central rings for all constrictor rings in the set have identical cross-sections although the diameter of their openings 14 are all different. By way of example and not limitation, the opening 14 in the central ring 11 of constrictor ring 10 is one inch in diameter. The number 10 constrictor ring is the largest of seven rings in the illustrative set. The diameter of the opening 14 in constrictor ring number 9 is 1/16 inch smaller than the opening in central ring having the number 10. Each constrictor ring in the set has a central ring whose diameter is 1/16 inch less than the next larger size ring so that in the series of seven constrictor rings 4-10, constrictor ring 4 has a central ring whose opening diameter is 10/16 inch or 5/8 inch. Experience has shown that at least seven rings whose openings are incremented in 1/16 inch steps are necessary to assure that a ring appropriate for most penis sizes is available for obtaining the most comfortable fit for the user. There is no need to provide a constrictor ring smaller than No.4 which has a central ring opening of 5/8 inch.

FIG. 2 shows a device whereby a penis may be exposed to vacuum so that the higher arterial blood pressure will cause blood to flow into the penis and stiffen it. A vacuum device similar to the one depicted in FIG. 2 is discussed in greater detail in U.S. Pat. No. 5,195,943 which issued to the inventor in the present patent application. In FIG. 2 one may see that the device comprises a tubular member 20 which is typically composed of a transparent synthetic resin. Tubular member 20 has a tubulation 21 which can be connected by way of a flexible tube 22 to a vacuum pump, not shown. The rim 23 of tube 20 is shown as being pressed against the body tissue 24 surrounding the base of the penis 25 which is presently inserted through the circular opening, not visible, which is defines by circular rim 23. The rim is pressed against body tissue 24 circumjacent the base of the penis so as to effect a vacuum seal between the rim and the body. The central ring 11 of one of the elastic constrictor rings is presently mounted on the end region of vacuum tube 20. When the erection has been obtained by exposure to the vacuum, the ring is slid from tube 20 and is deposited on the penis around its base. As in U.S. Pat. No. 5,195,943, the tube 20 has a rotatable sleeve 26 mounted to it. The sleeve has a beveled cam surface 27. The sleeve 26 is presently in a rotational position wherein cam surface 27 is bearing against a stationary boss 28 which is molded integrally with tube 20. The constrictor ring is forced off the vacuum tube 20 and deposited on the base of the penis by rotating sleeve 26. Rotation of the sleeve causes the camming surface 27 to react against stationary boss 28 such that the sleeve 26 advances axially and forces the constrictor ring off. Sometimes lubricants are used in contemplation of sexual intercourse. Lubricant can be on the hands of the user of the vacuum device at the time ejection sleeve 26 is to be rotated. To overcome the slippery effect of the lubricant, the sleeve is provided with a gripper rib 29 and the vacuum tube 20 is provided with a gripper rib 30. Rib 30, when gripped by the hand holds vacuum tube 20 against rotation while rib 29 when held by the other hand facilitates turning the sleeve 26 to deposit the constrictor ring onto the base of the penis.

There are two pieces of information which a potential user ought to possess before purchasing a vacuum device 20 and a set of constrictor rings as depicted in FIG. 1. First of all, the erect penis should fit into the opening surrounded by rim 23 of the vacuum tube with an appropriate clearance. The ideal situation is one where the diameter of the opening surrounded by rim 23 is about ¼ inch larger than the diameter of the base of the penis. If the penis insertion opening of the vacuum device has a diameter that is much larger than the diameter of the penis, there will be a substantial clearance between the penis and rim of the vacuum device such that tissue 24 surrounding the base of the penis can be pulled into the clearance opening by the vacuum developed in the vacuum tube 20. This is a painful experience for the user.

The practice, in accordance with the invention, is to make available to potential users a choice of at least three vacuum tubes 20 which have penis inlet openings varying in diameter in ¼ inch steps beginning with a diameter of 1.22 inches and ending with a diameter of 1.72 inches. Of course, a greater range of vacuum tube inlet opening sizes could be made available although the three sizes given will take care of the vast majority of the penis sizes. Most men will use No.5 or No.6 constrictor rings which have central ring opening diameters of ¹¹⁄₁₆ inch and ¾ inch. For the most part, there is no practical necessity for providing constrictor rings which have central ring openings whose diameters are less than ⅝ inches. On the other hand, it would be only for unusual special cases where a restrictor ring having a central ring opening diameter greater than 1 inch would be required. In any case, central ring size must be small enough so that when it is contracted it will permit entry of arterial blood into the penis under the influence of vacuum for massaging of the scrotum and no tighter than the user can tolerate without experiencing discomfort. Experience has shown that a properly selected ring for obtaining and maintaining an erection for 30 minutes or more is one that has central ring opening diameter of about 60 percent of the diameter of the erect penis.

In accordance with the invention, gauges are provided for gauging the diameter of the base of the penis in order to determine the size of the vacuum tube 20 and the constrictor ring sizes which are appropriate for the penis size. With the new gauging system, a man who is interested in compensating for the effects of impotency can be provided through the mail, on request, with a set of the gauges for the determining proper vacuum tube size, the proper constrictor ring size for sexually satisfying purposes and the proper ring size for securing a condom on a flaccid penis after sexual intercourse is terminated. The gauges can take the guesswork out of the constrictor ring selection process.

FIG. 4 shows a gauge that is calibrated for determining a penis diameter and relating it to the central ring size of the constrictor ring that should be selected for obtaining and maintaining an erection. The gauge is designated generally by the reference numeral 35. In practice, it is comprised of a thin but tough strip of paper. The strip has a distal end region 36 and a proximal end region 37. The proximal end region 37 has the configuration of a constrictor ring for artistic purposes but it should be understood that what appear to be holes in the central ring 38 and the loops 39 are not openings but are actually printed circles. The proximal end region 37 does, however, have a slot 40 which serves as a cursor as will be explained. The gauge is graduated in terms of constrictor ring sizes 2–12 which are beyond the range of the rings depicted in FIG. 1 at both extremities. An area 41 is available for printing information but is not needed for extending the lower end of the constrictor ring sizes since size less than number 2 is unlikely to be expected.

Figure 3:
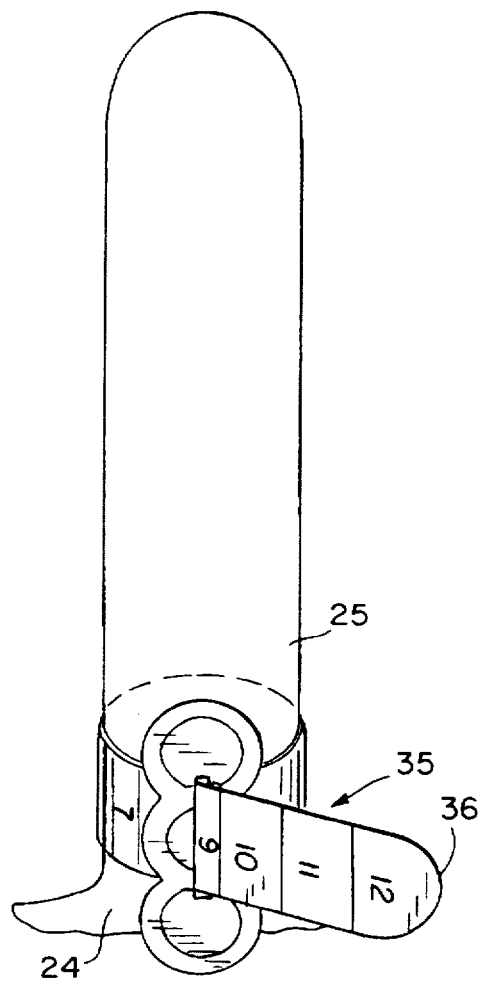
FIG. 3 is a perspective view of one of the new gauges wrapped around the penis to provide for reading an index number that identifies the constrictor ring size which is appropriate for the individual to obtain an erection by either the groin massaging method or the vacuum therapy method, for example.

FIG. 3 shows the gauge 35 of FIG. 4, for example, wrapped around the base of the penis with the distal end of the gauge strip passing through cursor slot 40 to provide a free end for facilitating drawing the gauge strip or band tightly on the base of the penis. Slot 40 will then coincide or overlay one of the graduations and will serve as a cursor for reading the graduation or ring size number from the gauge strip. In the FIG. 3 demonstration, the ring size No.9 is indicated by cursor slot 40. This means that there is a high probability that the No.9 constriction ring in the FIG. 1 set is an appropriate choice for the penis size in FIG. 3. If the cursor coincides with the mid-region of a marked off gauge zone such as the No.9 graduation, there is a high probability that the No. 9 ring will be suitable for that penis size. On the other hand, if the cursor slot lands on a line such as the line between graduations 9 and 10, or even beyond that line by a small amount, a No.9 constrictor ring would still be the proper choice. If the cursor slot 40 would coincide with the graduation line between graduations 9 and 8, for example, it would probably be most appropriate for the user to select a No.8 ring which is the smaller of the two ring sizes.

It should be recognized that the gauge 35 does not inform the user of the circumference or diameter of his penis in terms of inches or millimeters. The user simply reads a code number off a graduation which is indicated by the cursor slot when the gauge strip is wrapped around the base of the penis. The code number read from the gauge specifies selecting a constriction ring that has the same code number. The constriction ring of choice is not one that would have a central ring opening 14 whose diameter and circumference would be the same as those dimensions for the penis for if the central ring opening were of the same size as the penis diameter the ring would slide onto the penis and would not contract to control blood flow. Instead the gauge is calibrated such that the ring indicated to be selected by the gauge cursor slot is actually one which has a central ring opening whose diameter is a predetermined percentage of the penis diameter. Thus, the central ring diameter is smaller than the penis diameter so that after it is stretched and fitted on the penis the ring can contract and apply sufficient elastic force to control blood flow into and out of the penis. An actual embodiment of the FIG. 4 gauge is calibrated so that the unstretched opening 14 of the central ring in the constriction ring specified to be selected is equal to about 60% of true penis diameter. The preferred rings are composed of synthetic or natural latex and have a cross-sectional diameter of ¼ inch. This is appropriate for sexual intercourse where the erection is obtained by using a vacuum tube or by massaging the scrotum for example. However, the constriction rings provided by other manufacturers are likely to differ from the rings illustrative rings disclosed herein in cross-sectional diameter and in the elasticity of the material out of which the rings are constrictions are made so the ratio of the gauged size of the penis and the percentage of the diameter of the penis designed into the ring size may differ.

The gauge shown in FIG. 5 is structurally similar to the gauge shown in FIG. 4. The FIG. 5 gauge, however, is calibrated for assisting a male who desires to obtain an erection by using a vacuum device such as the one marked 20 in FIG. 2. As explained earlier, it is desirable for the vacuum device which is selected to have a penis entry opening surrounded by its rim 23 that is about ¼ inch larger in diameter than the diameter of the penis to overcome the problem of tissue being pulled into the vacuum device as the vacuum is increased. The gauge shown in FIG. 5 for selecting a vacuum device 20 having a penis entry opening of the correct size is designated generally by the reference numeral 45. The calibration or scale numbers on this gauge relate to the number designation or code of the opening size in the vacuum device that should be selected. The size of the calibration steps can be greater with this gauge, as shown, because the high degree of precision is not required for selecting a vacuum device penis entry opening which is defined by a rigid and inflexible rim 23. The underlying rule is that if the penis fits into the opening, the only parameter of interest is that the diameter of the penis inlet opening should not exceed the diameter of the penis by more than ¼ inch. The procedure for using the FIG. 5 gauge is the same as with the other gauges described herein. That is, the gauge is tightened on the penis as in FIG. 3 and the graduation number that is indicated by the cursor slot 40 is read. The user then selects a vacuum device that has the same number or is the closest one to the same number or code as was read from the gauge. This will identify a vacuum tube that has a penis entry opening which is at least about ¼ inch larger than the actual penis diameter.

The FIG. 6 embodiment of the gauge 55 is adapted for determining the proper ring for keeping the condom secured on the penis after the penis has become flaccid following completion of sexual intercourse. In this case it is appropriate for a constriction ring to be selected which will contract to the equivalent of 80% of the penis diameter. The scale 1-15 is calibrated to obtain that result. As with the other gauges, the user tightens the gauge 55 on the penis in accordance with FIG. 3 and reads the graduation number that is indicated by the cursor slot 40. The user then selects the constriction ring that has the same number in which case that constriction ring will have a central ring opening that is 20% smaller than actual penis diameter or, expressed in another way, the ring opening will be 80% of the penis diameter.

The gauge in FIG. 7 is one that has graduations for two different functions as presented in two adjacent columns. The left graduations, as the gauge is viewed in FIG. 7, is a repeat of the graduations on the FIG. 5 gauge and the right graduations are a repeat of the FIG. 6 gauge. In other words, the user can use the left gauge if ascertaining the proper vacuum tube is desired and can use the right gauge if ascertaining the proper condom retainer ring is desired. Of course, the gauges could also be on both sides of the strip but gauges made thus far have instructions for use printed on the side opposite of the side with the scale on it.

Although embodiments of the gauge have been described in detail, such description is intended to be illustrative rather than limiting, for the invention may variously embodied and is to be limited only by the claims which follow.

I claim:

1. A combination of a set of elastic penile rings and a gauge for selecting a ring from the set wherein each ring has an opening whose diameter when unstretched is a predetermined percent smaller than the diameter of the penis to which a ring selected from said set is to be applied, said rings in said set including a ring having the largest diameter opening and a ring having the smallest diameter opening and there is at least one ring in the set having an opening whose diameter is between said largest and smallest opening diameters, the rings having successive code indicia, respectively, for identification, said gauge comprising a strip of flexible material having distal and proximal ends and having a cursor slot at a distance from said distal end for the distal end to be passed through said cursor slot to form a loop for the strip to be grasped and pulled to tighten the loop on the penis, at least a part of said distance between said distal end and said cursor slot having graduations defining spaces which are identified in succession with code indicia corresponding to the code indicia that identify the rings to provide for a male who seeks a ring having an opening diameter that is said predetermined percent smaller than his penis diameter matching the code indicia indicated in a space between or on said graduations by coincidence of said cursor slot and said space or graduation, respectively, to thereby identify the ring diameter that is to be chosen without having to know the actual diameter of the penis or the diameter of the opening of the ring that is indicated to be chosen.

2. A combination of said set of elastic penile rings and a gauge according to claim 1 wherein the code indicia indicated by said cursor slot on said strip comprising said gauge when said strip is pulled tight on a penis corresponds to a code indicia on a ring in said set that has an opening diameter of about 60% of the actual diameter of said penis.

3. A combination of said set of elastic penile rings and a gauge according to claim 1 wherein the code indicia indicated by said cursor slot on said strip comprising said gauge when said strip is pulled tight on a penis corresponds to a code indicia on a ring in said set that has an opening diameter of about 80% of the actual diameter of said penis.

4. A combination of said set of elastic penile rings and a gauge according to claim 1 wherein said ring having the largest diameter opening in said set of rings has an opening diameter of about sixteen-sixteenths (16/16) of an inch.

5. A combination according to claim 4 wherein said ring having the smallest diameter opening in said set has an opening diameter of about ten-sixteenths (10/16) of an inch.

6. A combination according to claim 4 wherein said rings in said set constitute a series of rings wherein the next smaller diameter ring opening relative to said ring having the largest diameter opening is one-sixteenth (1/16) of an inch smaller and successive rings in the set have opening diameters declining in one-sixteenth (1/16) inch steps.

7. A combination of said set of rings according to claim 1 and another gauge wherein said another gauge is graduated for assisting a male contemplating use of a vacuum treatment chamber for developing an erection to select a penis insertion opening to the chamber having a diameter whose percent of the gauged penis diameter is equivalent to said penis insertion opening having a diameter that is about one-fourth (¼) inch greater than the diameter of the penis as determined with said another gauge.

8. An impotence treatment vacuum chamber having an opening through which the penis is inserted for being subjected to vacuum treatment, in combination with a penile gauge for assisting a male to select a chamber having said opening whose diameter exceeds the diameter of the penis by no more than a predetermined amount, the chamber having a cylindrical portion whose periphery adjacent said penis insertion opening is adapted for receiving an elastic penile ring for being slid from the device onto the penis when the penis is inserted and vacuum has been developed, said gauge comprising a strip of flexible material having distal and proximal ends and having a cursor slot at a distance from said distal end for the distal end to be passed through said cursor slot to form a loop for the strip to be grasped and pulled to tighten the loop on the penis, at least a part of said distance between said distal end and said cursor slot having graduations defining a series of spaces which are assigned code indicia that correspond to vacuum chamber diameters, respectively, such that when said loop is tightened on the penis said cursor slot will be coincident with a place on a said space on the strip comprising said gauge having an indicia that identifies a vacuum chamber having a penis insertion opening diameter that is appropriate for being selected.

9. A penile gauge according to claim 8 wherein the selected vacuum chamber is one that has an opening whose diameter exceeds the actual diameter of the penis by about one-quarter (¼) inch.

* * * * *